United States Patent [19]

Fletcher et al.

[11] Patent Number: 4,551,292

[45] Date of Patent: Nov. 5, 1985

[54] METHOD FOR MAKING A CATHETER WITH A SOFT, DEFORMABLE TIP

[75] Inventors: Bruce W. Fletcher, Plymouth; Mark A. Rydell, Excelsior; Edward W. Reese, Maple Grove, all of Minn.

[73] Assignee: Angiomedics, Inc., Plymouth, Minn.

[21] Appl. No.: 596,919

[22] Filed: Apr. 5, 1984

[51] Int. Cl.$^4$ .............................................. B29C 17/02
[52] U.S. Cl. .................... 264/139; 128/658;
264/162; 264/173; 264/232; 264/275; 264/292;
264/320; 264/322; 264/341; 425/318; 425/393;
604/280
[58] Field of Search ............... 264/292, 320, 322, 341,
264/139, 162, 173, 232, 275; 128/658; 604/96,
280, 281; 425/318

[56] References Cited

U.S. PATENT DOCUMENTS

| | | | |
|---|---|---|---|
| T872,012 | 3/1970 | Holt | 264/341 |
| 2,972,779 | 2/1961 | Cowley | 264/341 |
| 4,459,255 | 7/1984 | Sheridan | 264/320 |

FOREIGN PATENT DOCUMENTS

| | | | |
|---|---|---|---|
| 53-126078 | 11/1978 | Japan | 264/322 |
| 639997 | 7/1950 | United Kingdom | 264/320 |
| 986076 | 3/1965 | United Kingdom | 264/320 |

Primary Examiner—James Lowe
Attorney, Agent, or Firm—Orrin M. Haugen; Thomas J. Nikolai

[57] ABSTRACT

A method of forming a soft, deformable tip at the distal end of an elongated, flexible catheter made from a thermoplastic or elastomeric material in which the tip portion is first heated to soften the plastic and, subsequently, a specially prepared forming tool is inserted into the lumen of the catheter at the distal end and advanced to the point where an annular protuberance of a predetermined outside diameter is forced into the lumen so as to stretch and shape the plastic to conform to the forming tool. The distal end is then cooled and the forming tool removed, leaving a soft, collapsible segment integrally formed at the distal end of the catheter.

8 Claims, 11 Drawing Figures

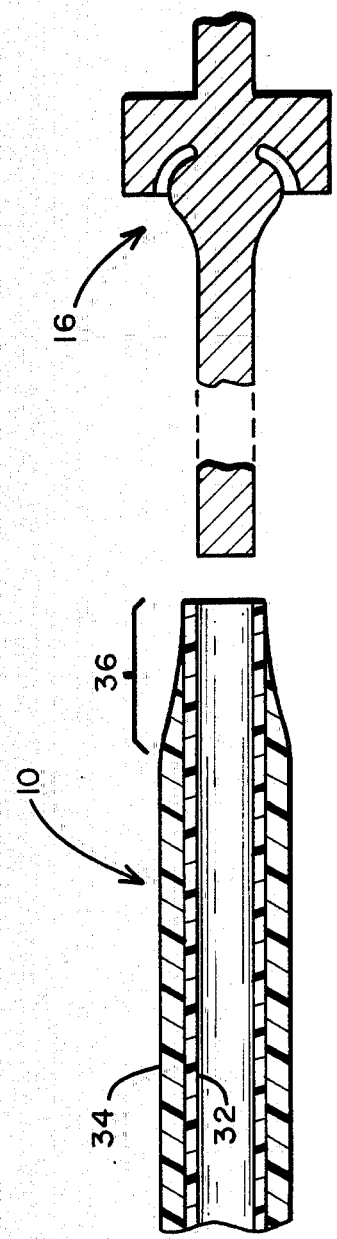
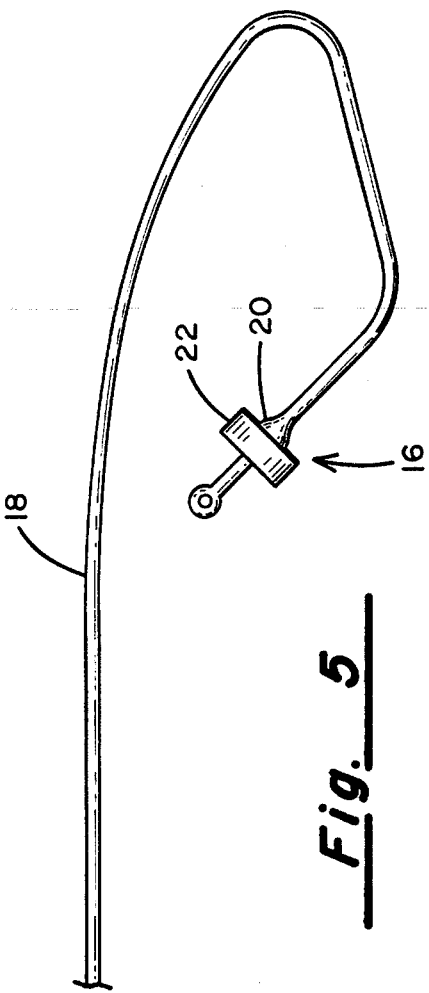
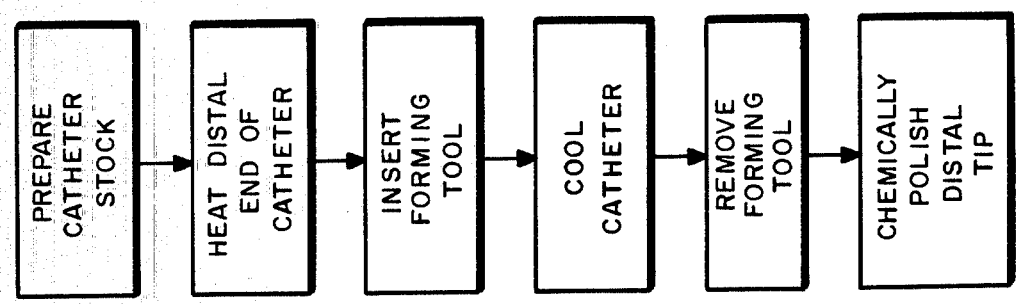

METHOD FOR MAKING A CATHETER WITH A SOFT, DEFORMABLE TIP

BACKGROUND OF THE INVENTION

I. Field of the Invention

This invention relates generally to methods of fabricating angiographic catheters or the like, and more particularly to methods of forming a soft, deformable tips at the distal end of such catheters.

II. Discussion of the Prior Art

In a co-pending patent application of Robert A. Van Tassel, et al, Ser. No. 520,996, filed Aug. 8, 1983, now Pat. No. 4,531,943, and assigned to the assignee of the instant application, there is described a catheter construction wherein a pre-molded soft, deformable tip is suitably bonded to the distal end of a catheter body so that when the catheter is later passed into the vascular system of a patient, there would be less trauma to the blood vessel occasioned by the introduction of the catheter. To create a smooth, yet reliable joint between the soft-tip member and the catheter body, it has been the practice to grind the exterior surface of the catheter body on a centerless grinder to create a zone of lesser thickness proximate the distal tip of the catheter stock and then to form a lap joint by fitting the pre-formed, soft-tip member onto the so-prepared end portion where it is held in place by a suitable adhesive or other known bonding technique. This process has proven to be somewhat slow and, considering the cross-sectional dimensions of angiographic catheters, slight variations in the wall thickness occurring during the centerless grinding operation can render the resulting catheter unacceptable, thus decreasing the manufacturing yield and increasing the per catheter cost.

The methods comprising the present invention allow the formation of the soft, deformable tip on the end of a catheter body in a comparatively inexpensive manner, while producing high yields of usable catheters.

SUMMARY OF THE INVENTION

In accordance with a first aspect of the invention, a tool, in the form of a cylindrical wire having a symmetrically-formed annular protuberance disposed thereon, is used. The O.D. of the wire is approximately equal to the diameter of the catheter's lumen while the annular bead exceeds this dimension. Next, the distal end of the catheter is subject to an elevated temperature until the thermoplastic material from which it is made reaches its softening point. Then, the forming tool is inserted into the lumen of the catheter at its distal end and is advanced into the lumen until the bead or protuberance enters the lumen to expand the thermoplastic material of the catheter body about the bead. Once the catheter body is so expanded, the distal tip portion is cooled, for example, by quenching, and the forming tool is then extracted, leaving a bulge of a predetermined shape proximate the distal tip of the catheter body.

In a variation of this inventive method, the catheter body is ground down at its distal end portion to form a taper of a predetermined angle. The tapered end is then placed in a mold and a suitable, low durometer plastic is molded onto the tapered portion of the catheter body. Next the forming wire with its annular protuberance is introduced into the molded end portion of the catheter and when properly positioned, the end portion, including the forming wire is heated, so as to take on the shape of the forming tool, and subsequently quenched. By properly shaping the bead or protuberance on the forming wire, it is possible to induce a preferential, circumferential fold-line in the stretched or expanded portion of the distal end of the catheter.

When the catheter mode in accordance with either of the above methods is later used in angiographic or related procedures, as the tip portion makes contact with a vessel wall or plaque build-up on such vessel wall, the tip portion tends to fold or collapse about the preferential fold-line, providing an increased area of contact and reduced pressure, all as is explained in the aforereferenced Van Tassel, et al patent application.

OBJECTS

It is accordingly a principal object of the present invention to provide simple and inexpensive methods for creating a soft, deformable tip on the distal end of an angiographic catheter.

Another object of the invention is to provide methods for forming a soft, deformable tip on the distal end of a catheter where the tip is made from a thermoplastic material different from that of the catheter body.

Yet another object of the invention is to provide a method for creating a soft, deformable tip element on the distal end portion of an angiographic catheter where the distal tip portion has predetermined profile and hardness characteristics.

Yet still another object of the invention is to provide a method for temperature-forming the distal end portion of an angiographic catheter so as to create a soft, deformable tip thereon.

These and other object and advantages of the invention will become apparent to those skilled in the art, from the following detailed description of a preferred embodiment, especially when considered in conjunction with the accompanying drawings in which like numerals in the several views refer to corresponding parts.

DESCRIPTION OF THE DRAWINGS

FIG. 1 is a process flow chart outlining the basic steps comprising one method in accordance with the present invention;

FIG. 3 illustrates an alternative arrangement for forming a soft, deformable tip at the distal end of the catheter in accordance with the present invention;

FIG. 5 illustrates the configuration of a forming wire typical of that which may be used in creating an angiographic catheter having a soft, deformable tip where the catheter is intended for use in cardiology.

DESCRIPTION OF THE PREFERRED EMBODIMENT

As is well known in the art, angiographic catheters are commonly introduced into the femoral artery and advanced through the vascular system so that radiopaque dyes or medicaments may be introduced at a predetermined site in the vascular system as a part of a diagnostic or treatment procedure.

Typically, such catheters comprise elongated, flexible plastic tubes having a diameter which is less than the cross-sectional size of the lumen of the blood vessel through which the catheter is to pass. Depending upon the target area to be probed, the distal end portion of the catheter may be bent or formed, for example, as in the Judkins catheter, to enhance the ability of the catheter to pass through an organ opening, such as the coronary ostium. Prior to the introduction on the market of catheter structures made in accordance with the aforereferenced Van Tassel, et al application, angiographic catheters normally have comprised a catheter body to which a distal end member of a predetermined shape configuration was attached. The catheter body typically comprised first and second concentrically disposed plastic tubular members having a braided, stainless steel sheath embedded therebetween so as to provide desired torque characteristics which allows the catheter to be better manipulated by applying forces at the exposed proximal end thereof. The tip portion was generally formed from a suitable thermoplastic material, e.g., polyurethane, which had been heat-set into a desired shape configuration for the purpose already alluded to above. Such prior art catheters typically had a blunt distal end. This relatively hard, blunt plastic tip of the prior art catheter had the potential of ripping through a blood vessel, requiring emergency procedures to repair the damage.

In efforts to avoid this type of accident, Dr. Van Tassel and his co-workers at Angiomedics, Inc. (applicants' assignee) devised a soft-tipped catheter which is more particularly described in the aforereferenced Van Tassel, et al patent application. The present invention is an extension of that earlier work and concerns manufacturing methods whereby a soft, deformable tip may be formed on the distal end of a plastic angiographic catheter in a fashion which is simpler and less expensive than the approach described in that earlier application.

Figure 2:
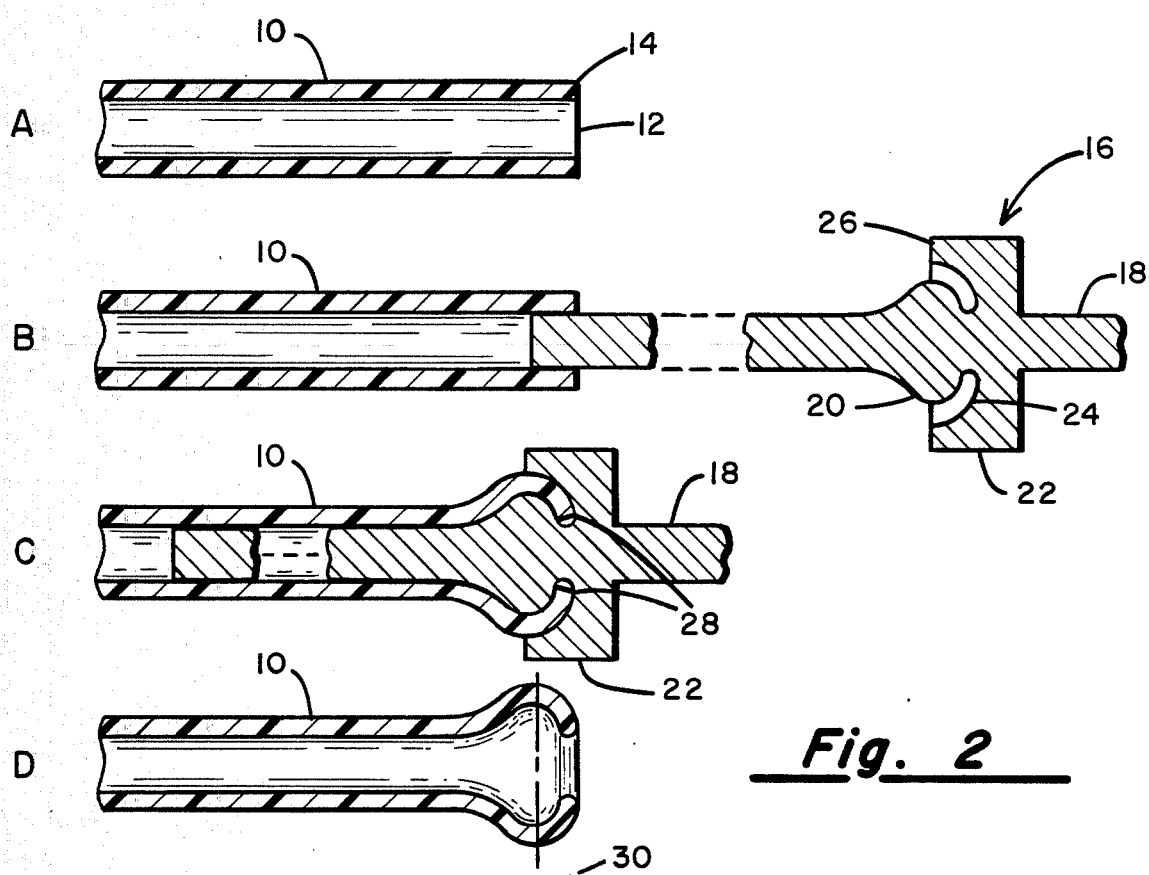
FIGS. 2A through 2D illustrate cross-sectional views of the distal end of a catheter during the tip-forming process in accordance with the method of FIG. 1.

Referring simultaneously to FIGS. 1 and 2, and in accordance with a first method, the first step is to prepare the catheter stock. This particular operation may involve known prior art methods, such as disclosed in the U.S. Pat. No. 3,585,707, which, when followed, yields a catheter body reinforced with stainless steel braid and terminating in a suitably bent and formed thermoplastic tip member. Typically, the tip will be formed from polyurethane, polyethylene or other suitable plastic or rubber matter. In any event, the distal tip portion 10 has a blunt end 12, typically having sharp edges as at 14, all as is shown in FIG. 2A.

Following the preparation of the catheter stock, the distal end portion may be heated until the softening point of the plastic tip is reached. This may typically be achieved by immersing a part of the distal end portion of the catheter into boiling water for a predetermined time. However, other heating methods may be used as well. This heating step is required only if the plastic of the tip is so hard that it cannot be spread by the forming tool used in the subsequent step.

Next, a forming tool indicated generally by numeral 16 is inserted into the heated end portion of the catheter as is illustrated in FIG. 2B. The forming tool itself comprises an elongated wire segment 18 having an annular bead or protuberance of a predetermined shape centered thereon, as at 20. In addition, a backstop member 22 having a concave recess 24 formed in the working face 26 thereof may be positioned a predetermined distance longitudinally from the protuberance 20 where the distance corresponds generally to the wall thickness of the tip member 10.

As the forming tool is advanced into the lumen of the pre-heated catheter, as shown in FIG. 2C, the distal tip portion thereof is stretched as it follows the contour of the protuberance 20 until it abuts the working face of the backstop member 22 such that further advancement causes the extreme tip portion of the catheter tip to completely fill the gap between the protuberance 20 and the concave face 24 of the backstop member. This configuration is clearly illustrated in FIG. 2C. The distal end portion of the catheter with the forming tool inserted therein may now again be heated so that the plastic will flow and conform to the shape of the forming tool.

Next, and as is indicated in the flow diagram of FIG. 1, the end of the catheter is cooled, such as by quenching in cold water, such that the plastic is made to take on the shape defined by the cooperating faces of the protuberance 20 and the backstop member 22.

The plastic from which the catheter tip is fabricated is sufficiently flexible so that the forming tool 16 may be extracted following the cooling step by applying a separating force between the catheter 10 and the forming tool 16. The view of FIG. 2D illustrates the configuration of the distal end of the catheter following the removal of the forming tool.

In that the above tip-forming process may still yield a catheter having sharp rather than rounded edges, especially at the point labeled 28 in FIG. 2C, as a final step, the tip of the catheter may be dipped in a suitable chemical solvent, such as two parts methylethylketone and one part tetrahydrofuran, which has the effect of dissolving and thereby rounding any such sharp edges.

The working surfaces of the forming tool, namely on the protuberance 20 and the backstop member 22, are such that a preferential, circumferential fold-line is formed along the broken line 30 and, as is explained in the aforereferenced Van Tassel, et al application, when the tip of the catheter is made to impinge upon a vessel wall surface or on any plaque deposits, the tip will tend to fold along that fold-line 30 to increase the effective area of the tip member and correspondingly reduce the pressure on the vessel which might otherwise result in the tearing of the vessel or the scratching of the delicate endothelial tissues lining the vessel.

FIG. 3 illustrates a variation in the method of forming a soft, deformable tip on the end of an angiographic catheter. Here, the tip portion 10 of the catheter body is formed in a co-extrusion process whereby an inner plastic or rubber tubular member 32 having a relatively low hardness (durometer), e.g., polyethylene, polyurethane, silicone rubber, is surrounded by a plastic or rubber coating 34 having higher hardness characteristics, e.g., polypropylene or polyurethane. As part of the first step illustrated in FIG. 1, the catheter body illustrated in FIG. 3 may be subjected to a centerless grinding operation so as to reduce the overall thickness of the outer layer 34 in the zone 36. In fact, if desired, the outer layer 34 may be ground completely away in the zone 36 so as to expose the lining 32 of the lower durometer material. When this catheter stock is so prepared and subjected to the remaining steps illustrated in the block diagram of FIG. 1, a catheter tip will result in which a material of a relatively low durometer has been formed so as to yield the tipped-shaped configuration as illustrated in FIG. 2D. Depending upon the plastic chosen for the inner member 32, it may be unnecessary to pre-heat the tip portion prior to the insertion of the forming tool because that softer plastic may have sufficient resiliency to allow the protuberance 20 to be forced into its lumen.

Figure 4:
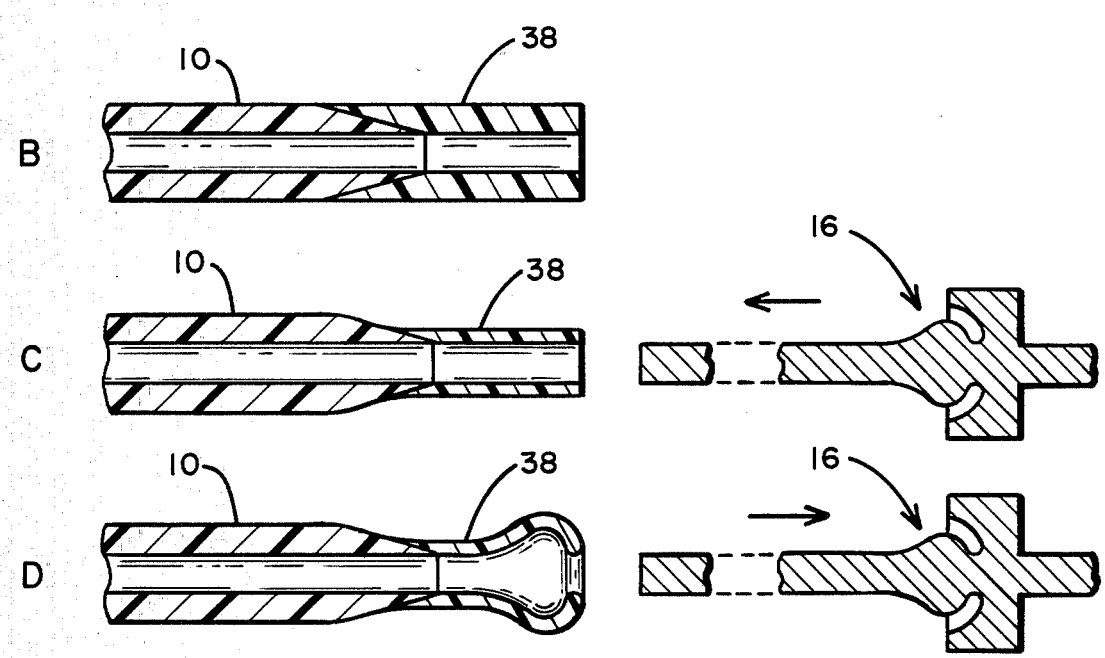
FIGS. 4A–4D illustrate another alternative method of forming a soft tip on the end of a catheter in accordance with this invention.

Referring next to FIG. 4, there is shown an alternate sequence of steps whereby the method of the present invention may be used to form a soft, deformable tip on the distal end of a catheter body. In accordance with this arrangement, the catheter stock is first ground down to form a frusto conical end portion as shown in FIG. 4A. The stock portion 10 may, for example, be formed from 55 durometer polypropylene which is relatively hard in comparison to the soft end tip yet to be formed. Next, the tapered end of the catheter stock 10 is inserted into a suitable mold and a plastic of a lower durometer is added to the mold to create a softer end portion 38 thereon. The end portion 38 may be formed from medical grade, low durometer urethane such as Type 80A material available from the Upjohn Company. Next, as is indicated in FIG. 4C, the end portion of the catheter is ground away on a centerless grinder which eliminates the appearance of any seams between the catheter stock 10 and the 80A material 38. Next, the procedure illustrated in FIG. 1 is carried out to form the bulbous end as shown in FIG. 4D. Because the tip portion being formed is made from the type 80A material, it is sufficiently soft that the pre-heating step illustrated in FIG. 1 is not necessary. That is to say, the forming tool 16 may be fitted into the lumen of the catheter as shown in FIG. 4C without having to pre-heat the material. Next, with the forming tool inserted, the end portion of the catheter may be heated as by immersion in boiling water such that the 80A material will soften and form about the protuberance of the forming tool in the matter already described. Then, the end portion of the catheter may be cooled as by quenching in water at room temperature and the forming tool extracted as shown in FIG. 4D, leaving a bulbous, soft, deformable tip on the distal end of the catheter.

FIG. 5 is intended to show that the forming tool 16 may be formed on or affixed to the same forming wire 18 as is used to create the desired bent configuration at the tip portion of an angiographic catheter, such as on the Judkin catheter used in cardiac environments. In this arrangement, the forming wire is inserted into the opening in the distal end of the catheter tip member and the catheter is threaded onto the forming wire 18 until its distal end engages the protuberance 20 and the backstop member 22, all has been previously explained. Now, when the tipped-end of the catheter is heated to the softening point and thereafter cooled, by quenching, not only will the end portion thereof be suitably bent in a desired fashion, but, also, the very tip end thereof will be expanded so as to create a soft, deformable tip element like that shown in FIG. 2D.

While the backstop member 22 helps to create a soft flexible bulbous tip on the end of the catheter, satisfactory results have been achieved with a forming tool which does not include the backstop member. Also, where the catheter material is sufficiently pliant, it is not necessary to heat the catheter end prior to inserting the forming tool. Heating subsequent to insertion, following by quenching, is sufficient to yield the desired tip configuration.

It is envisioned that various other changes and modifications may be made to the method and apparatus used in the practice of the method of th present invention without departing from the true spirit and scope thereof and, accordingly, the scope of the invention should be determined from the following claims.

What is claimed is:

1. A method of forming a soft, deformable tip on the distal end of a tubular thermoplastic or elastomeric catheter, comprising the steps of:
   (a) providing a tubular, thermoplastic or elastomeric catheter;
   (b) providing a forming tool having a cylindrical wire member of an outside diameter approximately equal to the diameter of the lumen of said tubular catheter and a protuberance of a predetermined shape symmetrically disposed on said wire member;
   (c) inserting said forming tool into the lumen of said catheter at its distal end;
   (d) advancing said forming tool into said lumen until said protuberance enters said lumen to expand the thermoplastic material about said protuberance;
   (e) heating said distal end of said catheter containing said protuberance to the softening point of the thermoplastic employed to create a preferential fold-line in the expanded portion of said distal end of said catheter;
   (f) cooling said distal end of said catheter below the softening point of the plastic; and
   (g) extracting said forming tool from said lumen.

2. The method as in claim 1 and further including the step of:
   (a) subjecting the expanded, distal tip of said catheter to a chemical polishing operation following the extraction of said forming tool.

3. The method as in claim 1 wherein said forming tool further includes a backstop member symmetrically disposed on said wire member and having a concave recess formed in the working face thereof, said concave recess forming a gap between itself and said protuberance, the gap corresponding to the thickness dimension of the wall of the catheter being worked upon.

4. The method as in claim 3 wherein said protuberance and said backstop member of said forming tool cooperate to form a toroidal reinforcement about the lumen of said catheter at its distal end when said forming tool is advanced into said lumen to the point where said distal end abuts said backstop member.

5. The method as in claim 1 and further including the step of first tapering the wall thickness of said tubular catheter proximate its distal end prior to the insertion of said forming tool into said lumen.

6. The method as in claim 1 and further including the step of pre-heating the distal end of said tubular thermoplastic catheter prior to the step of inserting said forming tool.

7. A method of fabricating a catheter with a soft, deformable tip as in claim 1 wherein said first listed step comprises:
   (a) co-extruding inner and outer elongated coaxial tubular members from differing thermoplastic materials having first and second hardness properties to a predetermined desired length, the softer of the two materials being surrounded by the harder of the two materials; and
   (b) grinding down the exterior surface of said outer material to a predetermined wall thickness proximate the distal end of said catheter.

8. A method for fabricating a catheter with a soft, deformable tip as in claim 1 wherein said first listed step comprises:
   (a) grinding a frusto conical end on an elongated thermoplastic tubular member;

(b) injection molding a tubular extension onto said frusto conical end, said tubular extension being of a softer thermoplastic material than said thermoplastic tubular member; and (c) grinding down the walls of at least a portion of said thermoplastic tubular member and said tubular extension proximate the juncture zone therebetween to a predetermined thickness.

* * * * *